United States Patent
Shen

(10) Patent No.: US 11,173,101 B1
(45) Date of Patent: Nov. 16, 2021

(54) SILVER ION BACTERIOSTATIC HAND SANITIZER AND PREPARATION METHOD AND APPLICATION THEREOF

(71) Applicants: LOOBI (GUANGZHOU) HEALTH INDUSTRY CO., LTD, Guangdong (CN); GUANGZHOU HWASUEN HEALTH INDUSTRY CO., LTD, Guangdong (CN)

(72) Inventor: Huazhong Shen, Guangdong (CN)

(73) Assignees: LOOBI (GUANGZHOU) HEALTH INDUSTRY CO., LTD, Guangdong (CN); GUANGZHOU HWASUEN HEALTH INDUSTRY CO., LTD, Guangdong (CN)

( * ) Notice: Subject to any disclaimer, the term of this patent is extended or adjusted under 35 U.S.C. 154(b) by 0 days.

(21) Appl. No.: 17/326,485

(22) Filed: May 21, 2021

(30) Foreign Application Priority Data

Jun. 23, 2020 (CN) .......................... 202010582337.3

(51) Int. Cl.
| | | |
|---|---|---|
| *A61K 8/23* | (2006.01) | |
| *A61Q 17/00* | (2006.01) | |
| *A61K 8/92* | (2006.01) | |
| *A61K 8/46* | (2006.01) | |
| *A61K 8/34* | (2006.01) | |
| *A61K 8/9789* | (2017.01) | |
| *A61K 8/362* | (2006.01) | |
| *A61K 8/86* | (2006.01) | |
| *A61K 8/37* | (2006.01) | |

(52) U.S. Cl.
CPC ................ *A61K 8/23* (2013.01); *A61K 8/345* (2013.01); *A61K 8/362* (2013.01); *A61K 8/37* (2013.01); *A61K 8/466* (2013.01); *A61K 8/86* (2013.01); *A61K 8/922* (2013.01); *A61K 8/9789* (2017.08); *A61Q 17/005* (2013.01); *A61K 2800/524* (2013.01); *A61K 2800/596* (2013.01); *A61K 2800/74* (2013.01); *A61K 2800/805* (2013.01)

(58) Field of Classification Search
None
See application file for complete search history.

(56) References Cited

FOREIGN PATENT DOCUMENTS

| | | |
|---|---|---|
| CN | 107468595 A | 12/2017 |
| JP | 2017048168 A | 3/2017 |

OTHER PUBLICATIONS

CN Office Action dated Oct. 10, 2020 in Chinese application (No. 2020105823373).
English translation of CN Office Action dated Oct. 10, 2020 in Chinese application (No. 2020105823373).
CN Notice of Allowance dated Jan. 26. 2021 in Chinese application (No. 2020105823373).
English translation of CN Notice of Allowance dated Jan. 26. 2021 in Chinese application (No. 2020105823373).
CN Search report dated Jun. 23, 2020 in Chinese application (No. 2020105823373).
English translation of CN Search report dated Jun. 23, 2020 in Chinese application (No. 2020105823373).
CN Office Action dated Dec. 3, 2020 in Chinese application (No. 2020105823373).
English translation of CN Office Action dated Dec. 3, 2020 in Chinese application (No. 2020105823373).
"Zhongzhi Silver ion hand sanitizer", recordation no. Yue G Zhuang wang bei No. 2020021827, Guangzhou Hwasuen Health Industry Co., LTD, website http://ftba.nmpa.gov.cn:8181/ftban/itownet/hzp_ba/fw/pz.jsp?processid=202002171157543vj22&nid=202002171157543vj22, first page.
Chinese language amendment/response filed in response to Office action dated Oct. 10, 2020 in Chinese application No. 2020105823373.
English translation of response filed in response to Office action dated Dec. 10, 2020 in Chinese application No. 2020105823373.
Chinese language amendment/response filed in response to Office action dated Dec. 3, 2020 in Chinese application No. 2020105823373.
English translation of amendment/response filed in response to Office action dated Dec. 3, 2020 in Chinese application No. 2020105823373.

*Primary Examiner* — David J Blanchard
*Assistant Examiner* — Sarah J Chickos
(74) *Attorney, Agent, or Firm* — McClure, Qualey & Rodack, LLP

(57) ABSTRACT

The present disclosure relates to the technical field of sanitary cleaning products, and more specifically to a silver ion bacteriostatic hand sanitizer and preparation method and application thereof. The silver ion bacteriostatic hand sanitizer is provided, including: 0.01~0.03 parts by weight of silver, 0.02~0.08 parts by weight of silver sulfate, 1~5 parts by weight of humectant, 10~18 parts by weight of skin conditioning agent, 0.3~0.8 parts by weight of preservative, 0.1~0.5 parts by weight of sodium dodecyl benzene sulfonate, 0.8~1.8 parts by weight of ethylhexylglycerol, 1~5 parts by weight of propylene glycol, 3~6 parts by weight of NONOXYNOL-14, 1~6 parts by weight of PEG-50 castor oil, 0.01~0.05 parts by weight of flavor and 80~120 parts by weight of deionized water. The silver ion bacteriostatic hand sanitizer has the advantages of high-efficiency bacteriostasis, sterilization and itching relief, mild performance and no stimulation, and keeps the hands moisturized.

1 Claim, No Drawings

SILVER ION BACTERIOSTATIC HAND SANITIZER AND PREPARATION METHOD AND APPLICATION THEREOF

TECHNICAL FIELD

The present disclosure relates to the technical field of sanitary cleaning products, and more specifically, to a silver ion bacteriostatic hand sanitizer and preparation method and application thereof.

BACKGROUND

Silver series bacteriostatic agents have a long history of application and have played a great role in human health. As far as safety and bacteriostatic effect are concerned, inorganic silver bacteriostatic agent and silver composite bacteriostatic agent have advantages of long-term effect, high efficiency, broad spectrum and safety. As early as in ancient times, people have found that silver has a natural bacteriostatic property and safety. At that time, the ancient Egyptians knew to cover the wound with a thin piece of silver to prevent bacterial infection and accelerate wound healing, and the Mongolians knew that goat's milk could be kept fresh with a silver container. In the Compendium of Materia Medica, Li Shizhen, a Chinese physician of the Ming Dynasty, records that silver filings have the functions of tranquilizing the five internal organs, calming the spirits, relieving the palpitations, and removing the pathogenic qi. The Chinese medicine uses the silver diagnosis to treat the related disease, and the Western medicine also has more than 100 years records with the silver treatment. It was found that silver has a very strong killing effect on various pathogenic bacteria such as *Escherichia coli* and *Staphylococcus aureus*, and the required concentration is very low, generally 10-6 (mass fraction) can be used for sterilization. In term of safety, silver is one of that constituents of human tissues, and cells treated with very low concentration of silver ions have no significant changes in cell aggregation, cell deformation, cell lysis, pH, etc. It can be seen that a small amount of silver ions on the human body no obvious harm. Therefore, the use of the silver series bacteriostatic agent in the improvement of the bacteriostatic function of textiles has sufficient safety.

Because inorganic bacteriostatic agents have the characteristics of broad-spectrum, long-lasting, safe and no drug resistance, people pay more and more attention to its research and application in many countries. The bacteriostatic mechanism of silver is summarized as follows: firstly, silver binds to the sulfhydryl group in the enzyme metabolized by pathogenic bacteria to inactivate the enzyme, so that the pathogenic bacteria cannot be metabolized and die; secondly, the silver reacts with the peptidoglycan exposed to the bacterial cell wall to form a reversible complex that prevents the transfer of oxygen into the cell, preventing the pathogen from moving and causing its death; thirdly, the silver ions combine with the DNA bases in the pathogenic bacteria, and form a cross-link with each other, leading to the denaturation of DNA structure, the inhibition of its replication, and the inactivation of pathogenic bacteria.

The root of human diseases comes from the contact of hands with bacteria, so hand disinfection and cleaning are very important, and it is an effective measure to prevent the spread of germs. Frequent hand washing is the most effective and simple way to control the spread of diseases and prevent infections. It has a good preventive effect on diseases transmitted by digestive tract and respiratory tract. And a large number of epidemiological investigations confirmed that the hand is an important way of nosocomial infection. Health care worker had severe bacterial contamination on their hands after nursing, diagnosis and treatment activities, and nosocomial infection can be transmitted directly or indirectly through the hands of health care workers, and this route is more dangerous than airborne transmission, leading to the spread of bacteria, resulting in infection rate of 30% of nosocomial infection.

Chinese patent application CN101766552A discloses a non-washable bacteriostatic hand sanitizer and a preparation method thereof. It includes 1~10 g of chlorhexidine salt, 5~1000 ug of silver nitrate, 30~90 ml of alcohol, 2~50 g of skin care agent, 0.5~3 g of tackifier, 0.5~3 g of surfactant, 0.5~5 g of p+H regulator and 15~50 ml of deionized water. However, that disinfection component of the product is single, and has no synergistic bacteriostatic effect and strong spectral bacteriostatic and bactericidal effects, and cannot be use for long-term bacteriostasis, and may generate certain irritation to the skin.

In order to solve that technical problems, it is necessary to provide a silver ion bacteriostatic hand sanitizer, which overcomes the defects of the traditional hand sanitize, and has the advantages of high-efficiency bacteriostasis, sterilization and itching relief, mild performance and no stimulation, and keeps the hands moisturized.

SUMMARY

In order to solve the problems in the prior art, a silver ion bacteriostatic hand sanitizer and preparation method thereof is provided. The silver ion bacteriostatic hand sanitizer provided by the present disclosure has good germicidal effect, has retention property, can kill virus, can continuously kill microorganisms escaping from skin, sweat gland and hair follicle, has mild performance, high stability and no stimulation, and can keep hand moisturized.

A silver ion bacteriostatic hand sanitizer is provided, including: 0.01~0.03 parts by weight of silver, 0.02~0.08 parts by weight of silver sulfate, 1~5 parts by weight of humectant, 10~18 parts by weight of skin conditioning agent, 0.3~0.8 parts by weight of preservative, 0.1~0.5 parts by weight of sodium dodecyl benzene sulfonate, 0.8~1.8 parts by weight of ethylhexylglycerol, 1~5 parts by weight of propylene glycol, 3~6 parts by weight of NONOXYNOL-14, 1~6 parts by weight of PEG-50 castor oil, 0.01~0.05 parts by weight of flavor and 80~120 parts by weight of deionized water.

Further, the silver ion bacteriostatic hand sanitizer is provided including: 0.02 parts by weight of silver, 0.05 parts by weight of silver sulfate, 3 parts by weight of humectant, 12 parts by weight of skin conditioning agent, 0.5 parts by weight of preservative, 0.3 parts by weight of sodium dodecyl benzene sulfonate, 1.2 parts by weight of ethylhexylglycerol, 3 parts by weight of propylene glycol, 4 parts by weight of NONOXYNOL-14, 4 parts by weight of PEG-50 castor oil, 0.02 parts by weight of flavor and 100 parts by weight of deionized water.

Further, the humectant is methyl propanediol.

Further, the skin conditioning agent includes licorice extract, *Artemisia annua* extract and sodium citrate in a weight ratio of 4~9:8~15:1~3.

Further, the skin conditioning agent includes licorice extract, *Artemisia annua* extract and sodium citrate in a weight ratio of 6:13:2.

Further, the preservative is phenoxyethanol.

In addition, a preparation method for the silver ion bacteriostatic hand sanitizer is provided, including:

S1: heating deionized water to 70~80□, stirring the heated deionized water and adding humectant, sodium dodecyl benzene sulfonate, ethylhexylglycerin, propylene glycol, NONOXYNOL-14 and PEG-50 castor oil into the heated deionized water at the same time to obtain a mixture, and stirring the mixture at a constant temperature for 20-30 min at a rotation speed of 800-1000 r/min until added humectant, sodium dodecyl benzene sulfonate, ethylhexylglycerin, propylene glycol, NONOXYNOL-14 and PEG-50 castor oil completely dissolved to obtain mixed solution I;

S2: cooling the mixed solution I obtained in step S1 to 20-30° C., adding silver, silver sulfate, skin conditioning agent, preservative and flavor into the mixed solution I, and homogenizing 20~60 min at a pressure of 8~15 MPa and a rotation speed of 2000~2500 r/min to obtain the hand sanitizer.

The main component of the skin conditioning agent added in the silver ion bacteriostatic hand sanitizer provided by the present disclosure is a plant extract, which effectively increases the bacteriostasis of the hand sanitizer, reduces the addition concentration of silver ions, and reduces the cost. The addition of silver ions not only increases the bacteriostasis spectrum but also increases the persistence of bacteriostasis, and the silver ions is used together with the added plant extract, which has good bactericidal effect and long bacteriostasis time.

The added *Artemisia annua* extract contains flavonoids, coumarins, terpenes, phenylpropanoic acid, volatile oil and other kinds of artemisinin, etc. It has the pharmacological actions of anti-malaria, anti-bacterium, anti-virus, anti-inflammation, antipyretic and analgesic, anti-schistosome and other parasites, immunity, tumor inhibition, and influence on cardiovascular system. In clinic, it is commonly used for the treatment of malaria, yin deficiency fever, bone steaming fever, heat pathogenic fever, chronic bronchitis, disk type lupus erythematosus, lichen planus of oral mucosa, dermatophytosis, neurodermatitis, pruritus cutanea, infantile autumn diarrhea, epistaxis and other symptoms. And the *Artemisia annua* decoction has stronger inhibition on *Staphylococcus epidermidis*, catarrh coccus, anthrax *bacillus*, diphtheria *bacillus*. The *Artemisia annua* decoction also has a certain inhibition on *Staphylococcus aureus*, green pus, dysentery, tuberculosis and other bacilli. The *Artemisia annua* volatile oil can inhibit all the dermatophytes at the concentration of 0.25%, and it has bactericidal effect at the concentration of 1%.

The licorice extract added is a medicinal component extracted from licorice. The licorice extract generally includes glycyrrhizin, glycyrrhizic acid, liquiritin, licorice flavonoid, back screen than sandalwood, prickly ash flower element, quercetin, etc. The utility model has the effects of tonifying spleen and invigorating qi, clearing heat and detoxicating, expelling phlegm and relieving cough, relieving urgency and relieving pain, and harmonizing various medicines. It is used for the treatment of spleen and stomach weakness, fatigue and weakness, palpitation and shortness of breath, cough and phlegm, abdominal cavity and limb pain.

In addition, a certain amount of sodium citrate is added in the skin conditioning agent, so that the stability of the *Artemisia annua* extract and the licorice extract can be increased, the bacteriostasis of the hand sanitizer can be effectively enhanced, and the obtained hand sanitizer has good stability. Frozen or heated hand sanitizer is reliable and does not delaminate.

Compared with the prior art, the silver ion bacteriostatic hand sanitizer is provided by the present disclosure with the following advantages:
(1) The silver ion bacteriostatic hand sanitizer provided by the disclosure has the functions of sterilization, decontamination, antibiosis and disinfection. The hand sanitizer is mild and low-irritation containing highly effective moisturizers which moisturize and keep the skin warm.
(2) The silver ion bacteriostatic hand sanitizer provided by the disclosure has good stability, no delamination phenomenon when being frozen and heated, is reliable in property, and achieves the sterilization effect of the chemical hand sanitizer. And it is easy and safe to use without toxic, stimulation or no bad smell.
(3) The silver ion bacteriostatic hand sanitizer provided by the present disclosure has good germicidal effect, has retention property, can kill virus, can continuously kill microorganisms escaping from skin, sweat gland and hair follicle, has mild performance, high stability and no stimulation, and can keep hand moisturized.

DETAILED DESCRIPTION OF EMBODIMENTS

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

The liquorice extract was purchased from Nanjing Bangnuo biotech Co., Ltd. and the *Artemisia annua* extract was purchased from Shanghai Lianmai Bioengineering Co., Ltd.

The remaining reagents used in the present disclosure are all common reagents and can be purchased from conventional reagent production and sales companies.

Embodiment 1 a Silver Ion Bacteriostatic Hand Sanitizer

The silver ion bacteriostatic hand sanitizer is provided including: 0.01 parts by weight of silver, 0.02 parts by weight of silver sulfate, 1 parts by weight of methyl propanediol, 10 parts by weight of skin conditioning agent, 0.3 parts by weight of phenoxyethanol, 0.1 parts by weight of sodium dodecyl benzene sulfonate, 0.8 parts by weight of ethylhexylglycerol, 1 parts by weight of propylene glycol, 3 parts by weight of NONOXYNOL-14, 1 parts by weight of PEG-50 castor oil, 0.01 parts by weight of flavor and 80 parts by weight of deionized water.

The skin conditioning agent includes licorice extract, *Artemisia annua* extract and sodium citrate in a weight ratio of 4:15:3.

The preparation method for the silver ion bacteriostatic hand sanitizer is provided, including:
S1: heating deionized water to 7011, stirring the heated deionized water and adding methyl propanediol, sodium dodecyl benzene sulfonate, ethylhexylglycerin, propylene glycol, NONOXYNOL-14 and PEG-50 castor oil into the heated deionized water at the same time to obtain a mixture, and stirring the mixture at a constant temperature for 20 min at a rotation speed of 800 r/min until added methyl propanediol, sodium dodecyl benzene sulfonate, ethylhexylglycerin, propylene glycol, NONOXYNOL-14 and PEG-50 castor oil completely dissolved to obtain mixed solution I;

S2: cooling the mixed solution I obtained in step S1 to 20° C., adding silver, silver sulfate, skin conditioning agent, preservative and flavor into the mixed solution I, and homogenizing 20 min at a pressure of 8 MPa and a rotation speed of 2000 r/min to obtain the hand sanitizer.

Embodiment 2 a Silver Ion Bacteriostatic Hand Sanitizer

The silver ion bacteriostatic hand sanitizer is provided including: 0.02 parts by weight of silver, 0.05 parts by weight of silver sulfate, 3 parts by weight of methyl propanediol, 12 parts by weight of skin conditioning agent, 0.5 parts by weight of phenoxyethanol, 0.3 parts by weight of sodium dodecyl benzene sulfonate, 1.2 parts by weight of ethylhexylglycerol, 3 parts by weight of propylene glycol, 4 parts by weight of NONOXYNOL-14, 4 parts by weight of PEG-50 castor oil, 0.02 parts by weight of flavor and 100 parts by weight of deionized water.

The skin conditioning agent includes licorice extract, *Artemisia annua* extract and sodium citrate in a weight ratio of 6:13:2.

The preparation method for the silver ion bacteriostatic hand sanitizer is provided, including:

S1: heating deionized water to 75□, stirring the heated deionized water and adding methyl propanediol, sodium dodecyl benzene sulfonate, ethylhexylglycerin, propylene glycol, NONOXYNOL-14 and PEG-50 castor oil into the heated deionized water at the same time to obtain a mixture, and stirring the mixture at a constant temperature for 25 min at a rotation speed of 900 r/min until added methyl propanediol, sodium dodecyl benzene sulfonate, ethylhexylglycerin, propylene glycol, NONOXYNOL-14 and PEG-50 castor oil completely dissolved to obtain mixed solution I;

S2: cooling the mixed solution I obtained in step S1 to 25° C., adding silver, silver sulfate, skin conditioning agent, preservative and flavor into the mixed solution I, and homogenizing 30 min at a pressure of 12 MPa and a rotation speed of 2300 r/min to obtain the hand sanitizer.

Embodiment 3 a Silver Ion Bacteriostatic Hand Sanitizer

The silver ion bacteriostatic hand sanitizer is provided including: 0.03 parts by weight of silver, 0.08 parts by weight of silver sulfate, 5 parts by weight of methyl propanediol, 18 parts by weight of skin conditioning agent, 0.8 parts by weight of phenoxyethanol, 0.5 parts by weight of sodium dodecyl benzene sulfonate, 1.8 parts by weight of ethylhexylglycerol, 5 parts by weight of propylene glycol, 6 parts by weight of NONOXYNOL-14, 6 parts by weight of PEG-50 castor oil, 0.05 parts by weight of flavor and 120 parts by weight of deionized water.

The skin conditioning agent includes licorice extract, *Artemisia annua* extract and sodium citrate in a weight ratio of 9:8:1.

The preparation method for the silver ion bacteriostatic hand sanitizer is provided, including:

S1: heating deionized water to 80□, stirring the heated deionized water and adding methyl propanediol, sodium dodecyl benzene sulfonate, ethylhexylglycerin, propylene glycol, NONOXYNOL-14 and PEG-50 castor oil into the heated deionized water at the same time to obtain a mixture, and stirring the mixture at a constant temperature for 30 min at a rotation speed of 1000 r/min until added methyl propanediol, sodium dodecyl benzene sulfonate, ethylhexylglycerin, propylene glycol, NONOXYNOL-14 and PEG-50 castor oil completely dissolved to obtain mixed solution I;

S2: cooling the mixed solution I obtained in step S1 to 30° C., adding silver, silver sulfate, skin conditioning agent, preservative and flavor into the mixed solution I, and homogenizing 60 min at a pressure of 15 MPa and a rotation speed of 2500 r/min to obtain the hand sanitizer.

Control Group 1 a Silver Ion Bacteriostatic Hand Sanitizer

The silver ion bacteriostatic hand sanitizer is provided including: 0.02 parts by weight of silver, 0.05 parts by weight of silver sulfate, 3 parts by weight of methyl propanediol, 12 parts by weight of skin conditioning agent, 0.5 parts by weight of phenoxyethanol, 0.3 parts by weight of sodium dodecyl benzene sulfonate, 1.2 parts by weight of ethylhexylglycerol, 3 parts by weight of propylene glycol, 4 parts by weight of NONOXYNOL-14, 4 parts by weight of PEG-50 castor oil, 0.02 parts by weight of flavor and 100 parts by weight of deionized water.

The skin conditioning agent includes licorice extract and sodium citrate in a weight ratio of 6:2.

The preparation method for the silver ion bacteriostatic hand sanitizer is similar to that of Embodiment 2.

The difference from Embodiment 2 is that no *Artemisia annua* extract is added to the skin conditioning agent.

Control Group 2 a Silver Ion Bacteriostatic Hand Sanitizer

The silver ion bacteriostatic hand sanitizer is provided including: 0.02 parts by weight of silver, 0.05 parts by weight of silver sulfate, 3 parts by weight of methyl propanediol, 12 parts by weight of skin conditioning agent, 0.5 parts by weight of phenoxyethanol, 0.3 parts by weight of sodium dodecyl benzene sulfonate, 1.2 parts by weight of ethylhexylglycerol, 3 parts by weight of propylene glycol, 4 parts by weight of NONOXYNOL-14, 4 parts by weight of PEG-50 castor oil, 0.02 parts by weight of flavor and 100 parts by weight of deionized water.

The skin conditioning agent includes licorice extract and *Artemisia annua* in a weight ratio of 6:13.

The preparation method for the silver ion bacteriostatic hand sanitizer is similar to that of Embodiment 2.

The difference from Embodiment 2 is that no sodium citrate is added to the skin conditioning agent.

Control Group 3 a Silver Ion Bacteriostatic Hand Sanitizer

The silver ion bacteriostatic hand sanitizer is provided including: 0.02 parts by weight of silver, 0.05 parts by weight of silver sulfate, 3 parts by weight of methyl propanediol, 12 parts by weight of skin conditioning agent, 0.5 parts by weight of phenoxyethanol, 0.3 parts by weight of sodium dodecyl benzene sulfonate, 1.2 parts by weight of ethylhexylglycerol, 3 parts by weight of propylene glycol, 4 parts by weight of NONOXYNOL-14, 4 parts by weight of PEG-50 castor oil, 0.02 parts by weight of flavor and 100 parts by weight of deionized water.

The skin conditioning agent includes licorice extract, *Artemisia annua* extract and sodium citrate in a weight ratio of 1:1:1.

The preparation method for the silver ion bacteriostatic hand sanitizer is similar to that of Embodiment 2.

The difference from Embodiment 2 is that the skin conditioning agent includes licorice extract, *Artemisia annua* extract and sodium citrate in a weight ratio of 1:1:1.

Test Example 1 Bacteriostatic Test

1. Test material: the silver ion bacteriostatic hand sanitizer prepared in Embodiment 1~3, Control group 1~3.
2. Test subjects: *Escherichia coli, Candida albicans, Staphylococcus aureus, Pseudomonas aeruginosa.*
3. Test methods: bacteriostatic experiment: 3 ml of the silver ion bacteriostatic hand sanitizer prepared for Embodiment 1~3 and Control group 1~3 was placed inside conical flasks respectively, and then 70 ml phosphate buffer (0.03 mol·L-1) and 5 ml bacteria solution were added, respectively, after the liquid was infiltrated into the medium, and after incubation at 37° C. for 2 min, colony counting was performed.

The bacteriostatic rate was calculated by the formula: $X=(A-B)/A\times100\%$, wherein X was the bacteriostatic rate, A was the average number of colonies before the test specimen was shaken, and B was the average number of colonies after the test specimen was shaken.

4. Test result

The test results are shown in Table 1.

TABLE 1

Results of the silver ion bacteriostatic hand sanitizer bacteriostatic test

| Group | Bacteriostatic rate (%) | | | |
| --- | --- | --- | --- | --- |
| | *Escherichia coli* | *Candida albicans* | *Staphylococcus aureus* | *Pseudomonas aeruginosa* |
| Embodiment 1 | >99.9 | >99.9 | >99.9 | >99.9 |
| Embodiment 2 | >99.9 | >99.9 | >99.9 | >99.9 |
| Embodiment 3 | >99.9 | >99.9 | >99.9 | >99.9 |
| Control group 1 | 64.31 | 65.17 | 66.17 | 52.19 |
| Control group 2 | 80.33 | 79.36 | 77.25 | 70.21 |
| Control group 3 | 82.66 | 83.57 | 83.74 | 77.32 |

It is known from Table 1 that the silver ion bacteriostatic hand sanitizer prepared in Embodiment 1~3 had more than 99.9% bacteriostatic rate against *Escherichia coli, Candida albicans, Staphylococcus aureus* and *Pseudomonas aeruginosa* within 2 min, indicating that the silver ion bacteriostatic hand sanitizer prepared in this work had good bacteriostatic effect. While the test results on the Control group 1~3 with the Embodiments showed that when the components of the skin conditioning agent provided by the present disclosure were changed, the bacteriostatic effect of the prepared silver ion bacteriostatic hand sanitizer within 2 min decreased obviously, indicating that the components of the skin conditioning agent provided by the present disclosure were indispensable and the synergy was obvious.

Test Example 2 Determination of Stability

1. Test material: the silver ion bacteriostatic hand sanitizer prepared in Embodiment 2, Control group 1~3.

2. Test contents: 5 g of the silver ion bacteriostatic hand sanitizer prepared in Embodiment 2, Control group 1~3, were placed into an incubator, all treated for 24 h and removed. When the temperature returned to room temperature, the results were observed.

3. Test result

The test results are shown in Table 2.

TABLE 2

Stability test results

| Testing condition | Group | Phenomenon |
| --- | --- | --- |
| Heat resistance (40 ± 1□) | Embodiment 2 | No turbidity, no floccule, uniform non-layered, no peculiar smell |
| | Control group 1 | Slight turbidity, no floccule, uniform non-layered, no peculiar smell |
| | Control group 2 | Serious turbidity, floccule, solution layered, no peculiar smell |
| | Control group 3 | Slight cloudiness, no floccule, uniform non-layered, no peculiar smell |
| Cold resistance (−5~0□) | Embodiment 2 | No turbidity, no floccule, uniform non-layered, no peculiar smell |
| | Control group 1 | Slight turbidity, no floccule, solution layered, no peculiar smell |
| | Control group 2 | Slight turbidity, floccule, solution layered, no peculiar smell |
| | Control group 3 | Slight turbidity, floccule, solution layered, no peculiar smell |

It can be known from Table 2 that under the detection conditions of heat resistance (40±1□) and cold resistance (−5~0□), the silver ion bacteriostatic hand sanitizer prepared in Embodiment 2 has no change in smell and color, no precipitation and suspended solids, and the texture is uniform, indicating that the hand sanitizer of the disclosure is in stable state. In the Control group 1~3, when the composition of skin conditioning agent was changed, the silver ion bacteriostatic hand sanitizer appeared turbid and flocculent, and the solution was layered under the same condition.

Described above are merely illustrative of the disclosure to enable those skilled in the art to implement or use the disclosure, and are not intended to limit the invention. It should be understood that any modifications, replacements or changes made by those skilled in the art without departing from the spirit of the disclosure should fall within the scope of the disclosure.

The invention claimed is:

1. A silver ion bacteriostatic hand sanitizer, comprising: 0.02 parts by weight of silver, 0.05 parts by weight of silver sulfate, 3 parts by weight of methyl propanediol, 12 parts by weight of skin conditioning agent, 0.5 parts by weight of phenoxyethanol, 0.3 parts by weight of sodium dodecyl benzene sulfonate, 1.2 parts by weight of ethylhexylglycerol, 3 parts by weight of propylene glycol, 4 parts by weight of NONOXYNOL-14, 4 parts by weight of PEG-50 castor oil, 0.02 parts by weight of flavor and 100 parts by weight of deionized water; and wherein the skin conditioning agent comprises licorice extract, *Artemisia annua* extract and sodium citrate in a weight ratio of 6:13:2.

* * * * *